(12) United States Patent
Liu et al.

(10) Patent No.: US 6,287,441 B1
(45) Date of Patent: Sep. 11, 2001

(54) MULTI-CONDITIONAL SSCP (SSCP$_5$): A RAPID METHOD FOR MUTATION SCANNING WITH VIRTUALLY 100% SENSITIVITY

(75) Inventors: Qiang Liu, Upland; Steve S. Sommer, Duarte, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/413,533

(22) Filed: Oct. 6, 1999

Related U.S. Application Data
(60) Provisional application No. 60/103,377, filed on Oct. 7, 1998.

(51) Int. Cl.[7] .................................................. G01N 27/26
(52) U.S. Cl. ........................................... 204/461; 204/466
(58) Field of Search .................................... 204/450, 451, 204/456, 466, 461

(56) References Cited

PUBLICATIONS

Schneider–Stock et al. ("Improved detection of P53 mutations in soft tissue tumors using new gel composition for automated nonradioactive analysis of single–strand conformation polymorphism", Electrophoresis (1997), 18(15), 2849–2851).*
Rubio et al. (Differentiation of citrus tristeza closterovirus (CTV) isolates by single–strand conformation polymorphism of the coat protein gene, Ann. Appl. biol. (1996), 12993), 479–489).*
Vasquez et al. (detection of polymorphism in the Trypanosoma cruzi tcP2.beta. gene family by single strand conformational analysis (SSCA)), Gene (1996), 180(1/2), 43–48.*
Birren, B.W. et al. "Optimized conditions for pulsed field gel electrophoretic separations of DNA", *Nucleic Acids Research* (1988); 16(15):7563–7582, Month unknown.
Johnson, P.H. and Grossman, L.I. "Electrophoresis of DNA in Agarose Gels. Optimizing Separations of Conformational Isomers of Double–and Single–Stranded DNAs" *Biochemistry* (1977); 16(19):4217–4225, Month unknown.
Landick, R. et al. "Optimization of Polyacrylamide Gel Electrophoresis Conditions Used for Sequencing Mixed Oligodeoxyribonucleotides" *DNA* (1984); 3(5):413–419, Month unknown.
Oto, M. et al. "Optimization of Nonradioisotopic Single Strand Conformation Polymorphism Analysis with a Conventional Minislab Gel Electrophoresis Apparatus", *Analytical Biochemistry* (1993); 213:19–22, Month unknown.

Raghava, G.P.S. "DNAOPT: A Computer Program to Aid Optimization of DNA Gel Electrophoresis and SDS–PAGE", *Bio–Techniques* (1995); 18(2):247–278, 280 (p. 279 is advertisment).
Velleman, S.G. "A Method for Empirically Optimizing the Detection of DNA Polymorphisms in Genomic DNA by Denaturing Gradient Gel Electrophoresis", *Bio Techniques* (1992); 12(4):521–524.
Kukita, Y., et al. "SSCP Analysis of Long DNA Fragments in Low pH Gel", Month unknown *Human Mutation*, 1997; 10:400–407.
Liu, Q., et al. "Bi–directional dideoxy fingerprinting (Bi–ddf): a rapid method for quantitative detection of mutations in genomic regions of 300–600 bp", *Human Molecular Genetics*, Month unknown 1996; 5(1):107–114.
Liu, Q. and Sommer, S. "The SSCP Phenomenon: Addition of HEPES Buffer Dramatically Affects Electrophoretic Mobility", *Bio Techniques*, Jul. 1998; 25(1):50–56 (4 pages).
Sasaki, T. et al. "ATM Mutations in Patients With Ataxia Telangiectasia Screened by a Hierarchical Strategy", *Human Mutation*, Month unknown 1998; 12:186–195.

\* cited by examiner

*Primary Examiner*—Jill Warden
*Assistant Examiner*—Alex Noguerola
(74) *Attorney, Agent, or Firm*—Rothwell, Figg, Ernst & Manbeck

(57) ABSTRACT

Experiments were performed to test for a set of SSCP conditions that would detect virtually all mutations in a nucleic acid being analyzed. The effects of buffer, gel matrix, temperature, and additive were all tested. Dideoxy fingerprinting was used as a tool to generate a large statistical sample (about 1,500) of mutation-containing single-stranded segments in order to evaluate adequately the sensitivity under a given condition. Mutations in exons H and B/C of the factor IX gene were utilized. SSCP sensitivity, as conveniently measured by the average SSCP efficiency, varied with conditions. Correlation coefficients (R) identified pairs of conditions that were either close to independent or complementary. Five conditions were selected with sufficient redundancy to detect all the mutations in the set tested. The sensitivity of multi-conditional SSCP (SSCP$_5$) was determined by blinded analyses on samples containing mutations in all the eight exon regions in the factor IX gene. All of the 84 single-base substitutions were detected in the blinded. 90% of these mutations were detected by more than one condition. SSCP$_5$ is estimated to be five times faster than fluorescent DNA sequencing for the detection of virtually all mutations when the five conditions are applied.

19 Claims, 5 Drawing Sheets

MULTI-CONDITIONAL SSCP (SSCP$_5$): A RAPID METHOD FOR MUTATION SCANNING WITH VIRTUALLY 100% SENSITIVITY

CROSS REFERENCE TO RELATED APPLICATIONS

This application is related to U.S. Provisional Application Serial No. 60/103,377 filed Oct. 7, 1998.

BACKGROUND OF THE INVENTION

Single-strand conformation polymorphism (SSCP) is the most widely used method for mutation scanning. With SSCP, single-base sequence changes can be detected by altered electrophoretic migration of one or both single strands on a non-denaturing gel. SSCP does not detect all sequence changes with one electrophoresis condition and its sensitivity is a complex function of sequence context and size (Glavac and Dean, 1993; Hayashi and Yandell, 1993; Hongyo et al., 1993; Liu and Sonuner, 1994; Michaud et al., 1992; Sarkar et al., 1992a; Sarkar et al. 1992b; Sheffield et al., 1993; Takahashi-Fujii et al., 1993).

Previous work suggested that the idiosyncratic nature of SSCP sensitivity is a function of both the distribution of mobility of single-base changes and the mobility of the wild type sequences relative to that of all single-base changes (see FIG. 1). For a 200 bp segment, there are 600 possible variants that differ by a single-base substitution. If it were possible to generate all 600 possible variants and to plot the mobility in units of band widths, it is apparent that the sensitivity of SSCP will be less for a segment in which the mobility of the wild type sequence is close to the mode (see FIG. 1A). If the variance of mobility is wider (FIG. 1B), SSCP sensitivity, on average, will be higher than with the first condition. However, this is not necessarily so, because the location of the wild type sequence within the distribution is also critical.

At least two ways to increase the sensitivity of SSCP have been described. In one approach, SSCP is hybridized with another method in order to generate the redundancy of mutation-containing segments necessary to detect virtually all mutations. For example, in dideoxy fingerprinting (ddF), SSCP is combined with Sanger dideoxy sequencing (Lin and Sommer, 1994; Sarkar et al., 1992b). SSCP can also be combined with restriction endonuclease fingerprinting (REF) (Liu and Sommer, 1995) and with bi-directional dideoxy fingerprinting (bi-ddF) (Liu et al., 1996). A Sanger dideoxy termination reaction is performed with one dideoxy terminator. The terminated single-stranded segments are electrophoresed through a non-denaturing gel. The ladder of segments subsequent to the mutation contain the same mutation with different 3' ends. In a second approach, SSCP is performed under two or more conditions. Typically, two temperatures are utilized, and occasionally, two temperatures with and without glycerol (Glavac and Dean, 1993; Liu and Sommer, 1994).

Recently, we reported that the pattern of SSCP shifts varied markedly when HEPES was added to standard TBE buffer (Liu and Sommer, 1998). The correlation coefficient (R) between these two conditions was 0.46. These results hint that sugar/base and sugar/sugar interactions are more important than secondary structure, which should not be much affected by the addition of HEPES.

Herein, we report a detailed analysis of gel matrix, running buffer, temperature, and additive to search for a set of sensitive and complementary electrophoretic conditions for SSCP analysis. ddF was utilized in order to provide a very large sample of mutation-containing segments for analysis. From the data, five conditions were chosen and SSCP$_5$ analysis was performed with 100% sensitivity in two blinded analyses.

The publications and other materials used herein to illuminate the background of the invention or provide additional details respecting the practice, are incorporated by reference, and for convenience are respectively grouped in the appended List of References.

SUMMARY OF THE INVENTION

Experiments were performed to test for a set of SSCP conditions that would detect virtually all mutations in a nucleic acid being analyzed. The effects of buffer, gel matrix, temperature, and additive were all tested. Dideoxy fingerprinting was used as a tool to generate a large statistical sample (about 1,500) of mutation-containing single-stranded segments in order to evaluate adequately the sensitivity under a given condition. Mutations in exons H and B/C of the factor IX gene were utilized. SSCP sensitivity, as conveniently measured by the average SSCP efficiency, varied with conditions. Correlation coefficients (R) identified pairs of conditions that were either close to independent or complementary. Five conditions were selected with sufficient redundancy to detect all the mutations in the set tested. The sensitivity of multi-conditional SSCP (SSCP$_5$) was determined by blinded analyses on samples containing mutations in all the eight exon regions in the factor IX gene. 2.5 kb of factor IX gene sequence were scanned in one lane by 15 PCR-amplified segments (125 kb of sequence scanned per gel). All of the 84 single-base substitutions were detected in the blinded analyses, the first consisting of 50 hemizygous mutant and wild type samples and the second consisting of 50 heterozygous mutant and wild type samples. 90% of these mutations were detected by more than one condition. SSCP$_5$ is estimated to be five times faster than fluorescent DNA sequencing for the detection of virtually all mutations when the five conditions are applied.

BRIEF DESCRIPTION OF THE FIGURES

FIG. 2A shows the results of ddF performed on 29 patients with hemophilia B and a wild type sequence (Lane C). The conditions used were PAGE/TRI/20° C. It should be noted that RT in the figures means room temperature which was 20° C. FIG. 2B is the same as for FIG. 2A except that the conditions used were PAGE/CAP/20° C. For both 2A and 2B, the location of segments of specific size was determined by the absence of a normal band or the presence of additional bands which occurred in about half of the mutations (informative dideoxy component). These bands facilitated the analysis of the gel by finding the mobility of segments of certain defined sizes. For both FIGS. 2A and 2B lanes marked C are a wild type DNA and lanes 1–29 are mutant samples from patients with hemophilia B. The efficiency of the SSCP component is indicated on the gel top for each mutation analyzed.

DETAILED DESCRIPTION OF THE INVENTION

Figure 1B:
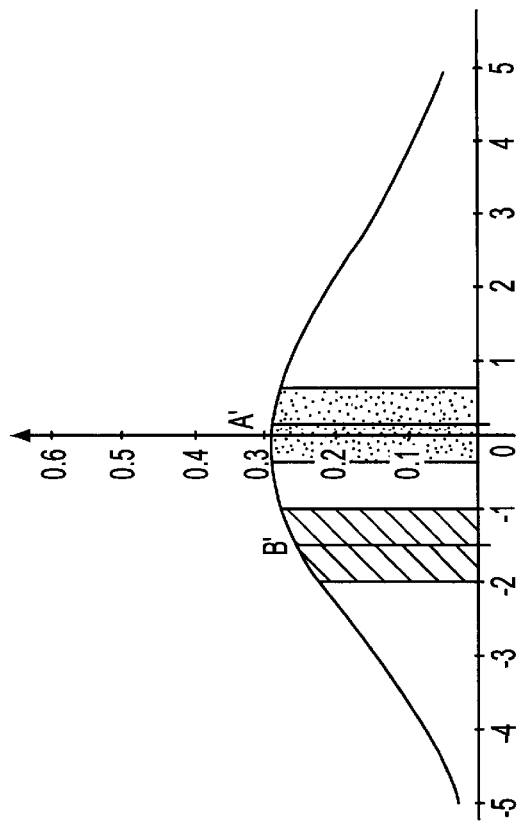
FIGS. 1A–B are schematics of the principle of SSCP sensitivity. The X-axis represents segment mobility in units of band thicknesses from the average of mobilities. The mobility of two segments can be distinguished if they differ by a thickness of more than one-half of a band. The Y-axis shows the relative frequencies of segments at a given mobility. The mobility of two hypothetical wild type sequences are indicated by A' and B', respectively, FIGS. 2A–C.
Figure 1A:
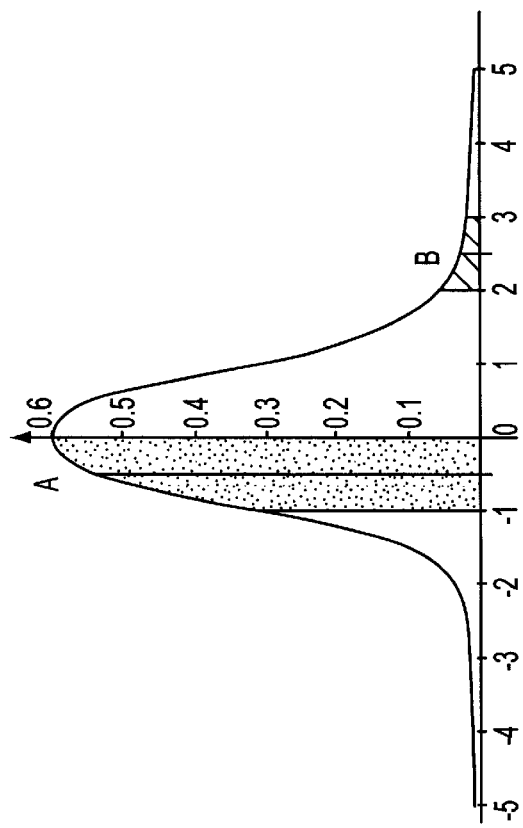

Experiments were performed to search for sensitive and complementary conditions for performing SSCP which will detect a greater number of mutations than is seen when standard SSCP methods are utilized. ddF gels were utilized to efficiently explore the SSCP sensitivity of different conditions. Exons H and B/C of the factor IX gene were studied. For a given mutation, the efficiency of the SSCP component is the percentage of mutation-containing segments which are shifted. The segments of the SSCP components of up to 300 bases were scored. The number of the mutation-containing segments varied from 1–46, depending on the location of the mutation. The efficiency of the SSCP component was utilized as a measure of the likelihood that a given mutation would show a detectable shift in mobility under a given condition. For the few samples in which the number of mutation-containing segments was low (fewer than 13), the results were generally similar when the analysis was extended to include segments up to 350 nucleotides.

To explain efficiency more fully, a hypothetical example is presented. On average, a tY nucleic acid of 300 bases or more will show 300/4 or 75 segments in a single sequencing lane using a single labeled nucleotide when looking only at the first 300 bases. For this hypothetical example, assume that there are 75 bands or segments and further assume that the nucleic acid has a mutation at base 22 which is in the 6th segment from the bottom of the gel. In such an instance segments 1–5 are fully wild type and segments 6–75 (a total of 70 segments) will include the mutation. If it is seen that 56 of the segments are shifted, then the efficiency is calculated as (56/70)(100)=80%. If instead the mutation is not at base 22 but rather at base 242 which is in the 61st segment, then the mutation will be present in only segments 61–75 (a total of 15 segments). If it is seen that 9 of these segments are shifted, then the efficiency is (9/15)(100)=60%.

The present invention is further detailed in the following Examples, which are offered by way of illustration and are not intended to limit the invention in any manner. Standard techniques well known in the art or the techniques specifically described below are utilized.

EXAMPLE 1 ddF in Two Regions

A 785 bp region of exons B/C of the factor IX gene was amplified with primers F9(6094)-30D and F9(6878)-27U and a 1 kb region of exon H of the factor IX gene was amplified with primers F9(30646)-34D and F9(31645)-31U. Primers are named as described in Yoshitake et al. (1985). For example, F9(6094)-30D is an oligonucleotide in which the 5' end begins at basepair 6094, the length is 30 bases, and the orientation is downstream (D), i.e., in the direction of transcription. The precise sizes and locations of the amplified segments and the dideoxy termination segments can be obtained from the informative names. The nucleotide sequence of the gene for human factor IX (anti-hemophilic factor B) is found in Yoshitake et al. (1985). PCR was performed at 94° C. for 15 seconds, 55° C. for 30 seconds, and 72° C. for three minutes for 30 cycles. The PCR mixture contained a total volume of 50 µL of 50 mM KCl, 10 mM Tris/HCl, pH 8.3, 1.5 mM $MgCl_2$, 200 µM of each DNTP, 0.1 µM of each primer, 1 unit of Taq (BMM), and 500 ng of genomic DNA.

ddF reaction was performed with Thermo Sequenase radiolabeled terminator cycle sequencing kit (Amersham Life Science). The sequencing mixture contained a total volume of 7 µL of 16.7 mM Tris/HCl, pH 9.5, 4.2 mM $MgCl_2$, 2.1 µM of each dNTP, 0.021 µM of [$\alpha$-$^{33}$P]ddCTP or [$\alpha$-$^{33}$P]ddGTP (1500 Ci/mmol, 450 Ci/mL), 1.8 units of Thermo Sequenase DNA polymerase, 200 ng of purified PCR product and 0.1 µM of sequencing primer F9(6272)-22D for exons B/C or F9(30851)-19D for exon H. Denaturation was at 95° C. for 15 seconds, annealing was at 55° C. for 30 seconds and elongation was at 72° C. for one minute for a total of 30 cycles. 15 µL of stop/loading buffer (50% formamide, 7 M urea, 2 mM EDTA, 0.05% bromophenol and 0.05% xylene cyanol) was added to each tube.

Figure 2A:
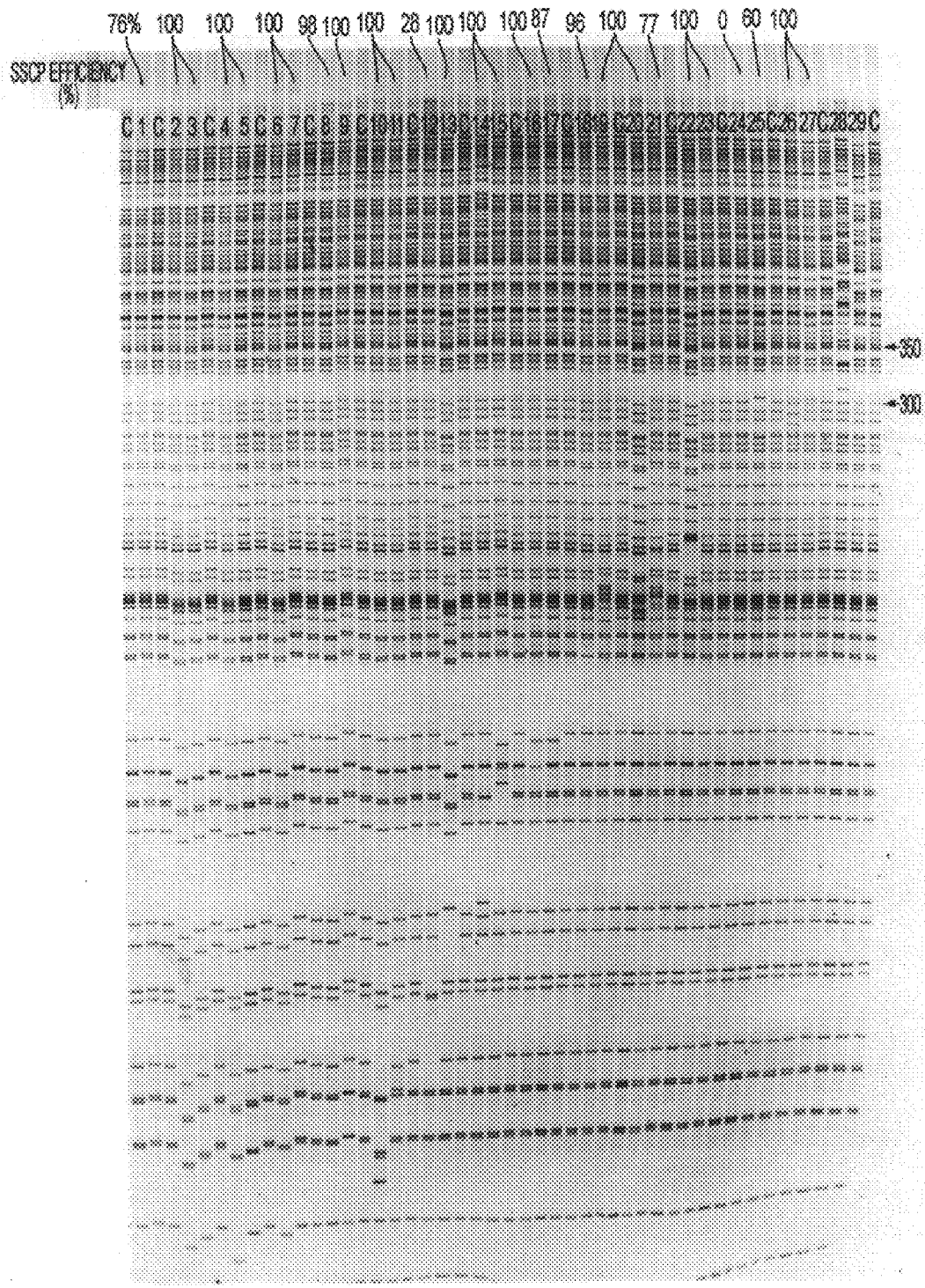
FIGS. 2A–B show the results of ddF in exon H of the factor IX gene using two different buffers.
Figure 2B:
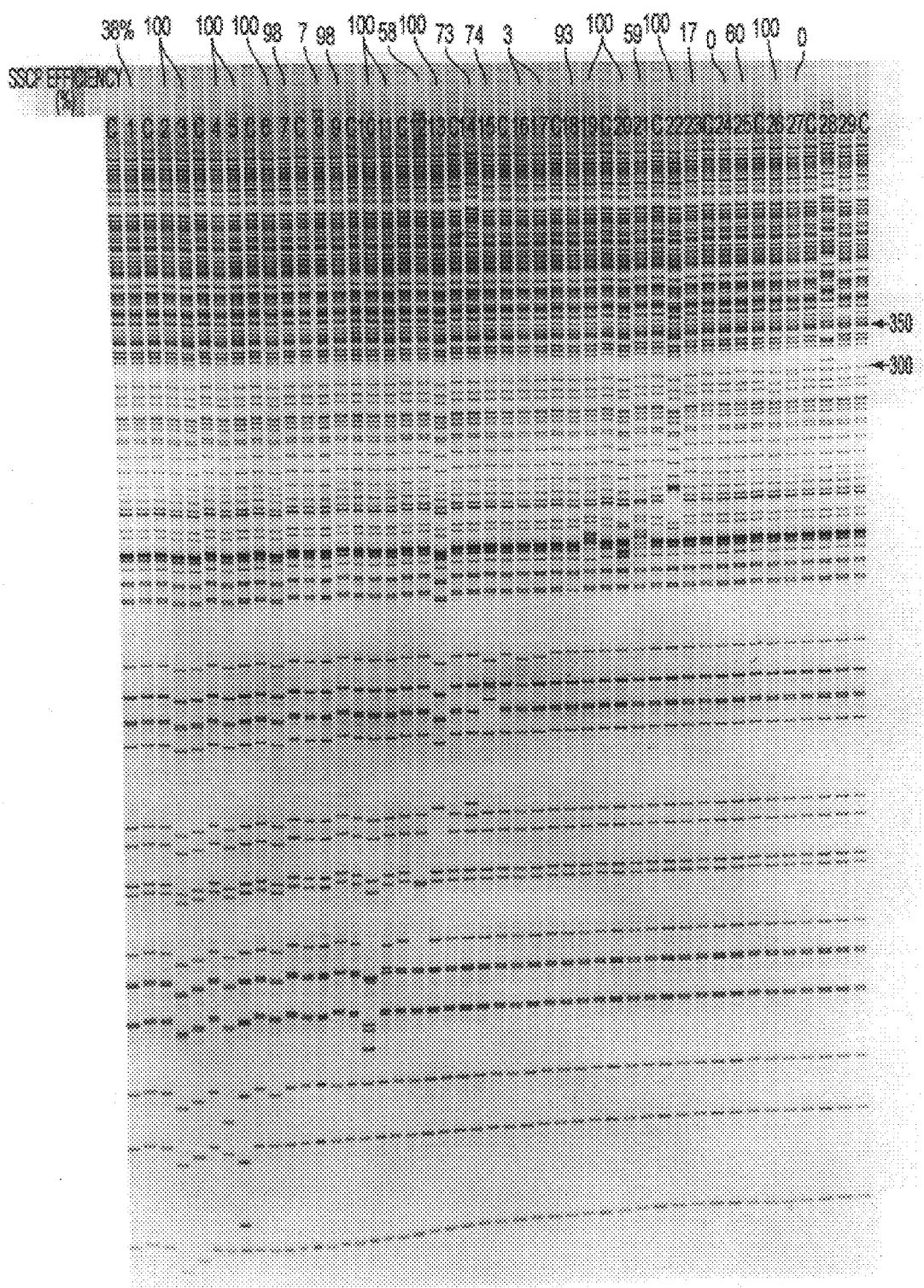
Figure 2C:
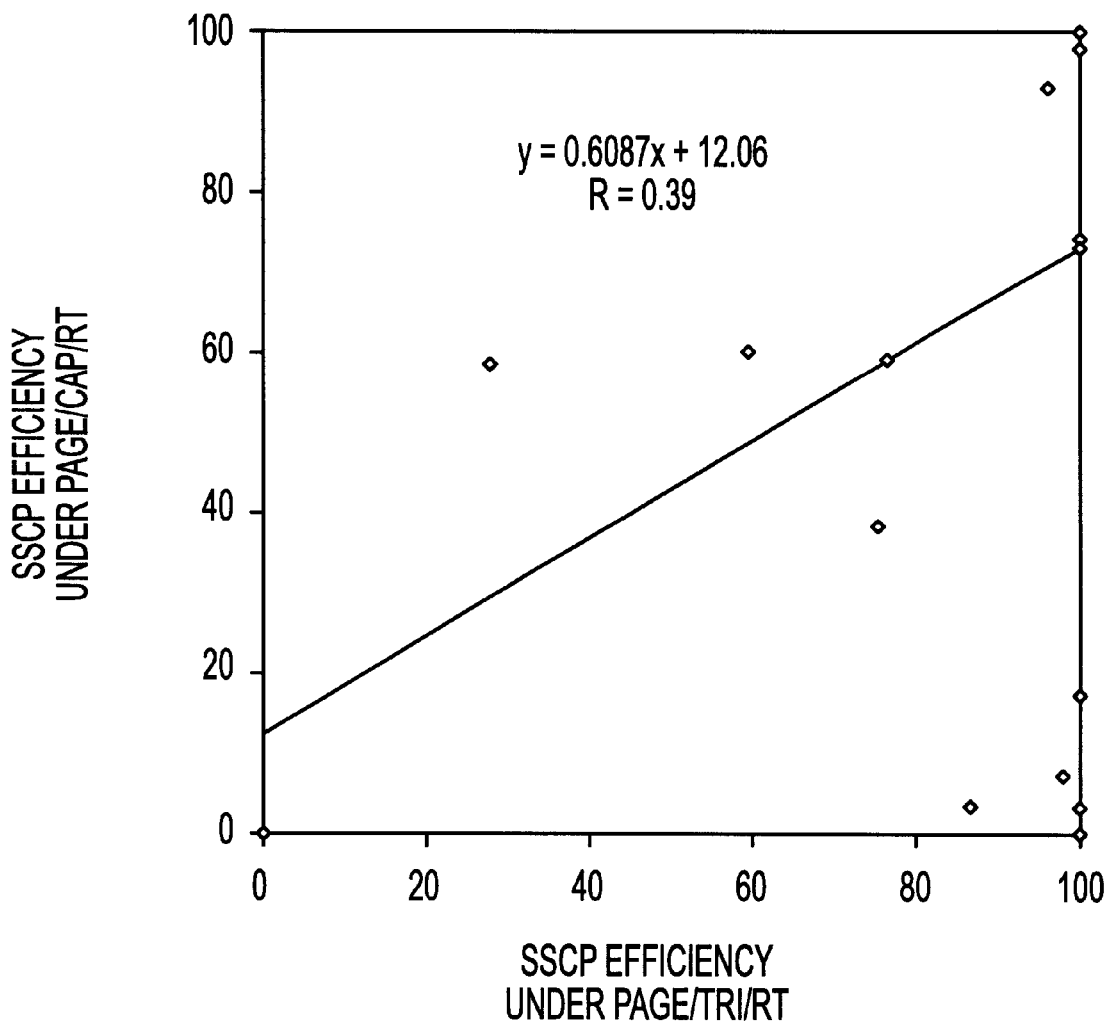
FIG. 2C is a mapplot showing the correlation of the SSCP efficiency between two conditions in exon H of the factor IX gene. Twenty-four mutations in exon H were analyzed. The X-axis represents the efficiency of the SSCP component (%) for a specific mutation under the condition of PAGEPHU/20° C. The Y-axis represents the corresponding efficiency (%) for the same mutation under the condition of PAGE/CAP/20° C. For each mutation, the efficiency is the ratio of the number of shifted mutation-containing segments to all the mutation-containing segments in SSCP component.
Figure 3:
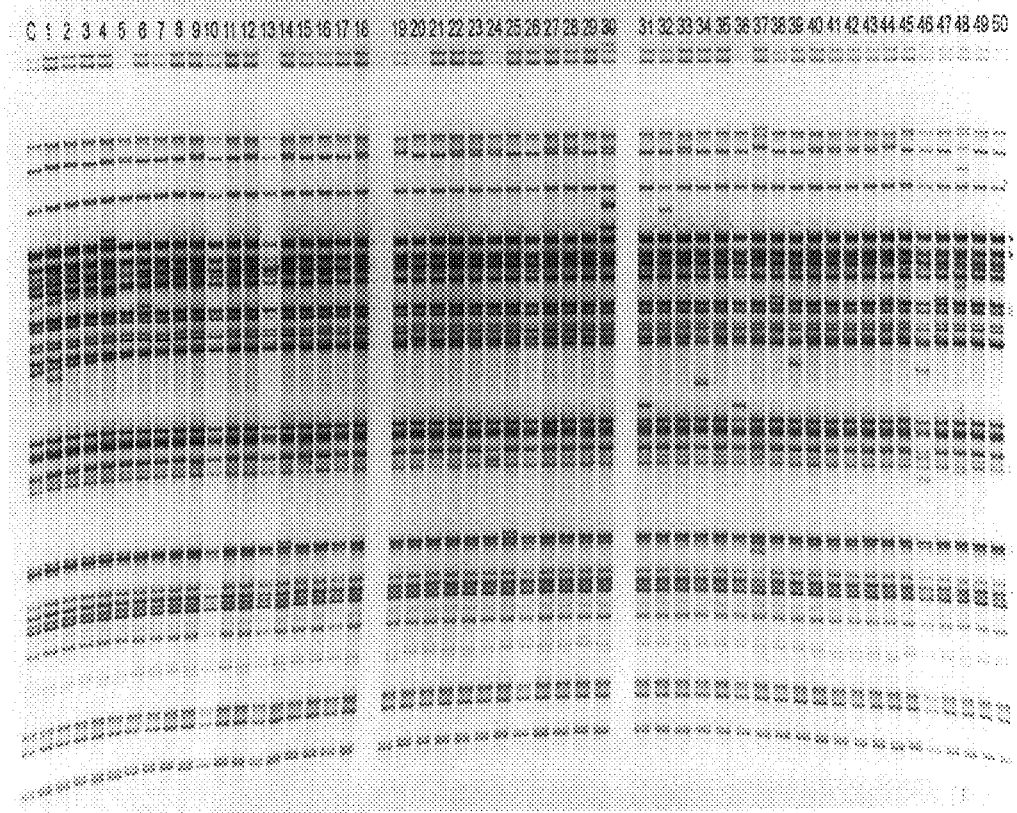
FIG. 3 shows the results of a blinded analysis of SSCP. The samples were analyzed for the factor IX gene with PAGEMW20° C. Lane C is a wild type sample and lanes 1–50 are blinded samples containing heterozygous mutations.

29 mutations in exon H of the factor IX gene were utilized. The sample numbers and associated mutations correspond to the lane numbers for FIGS. 2A and 2B. The mutations are numbered as described in Yoshitake et al. (1985). For example, the mutation named C30875T is a C to T mutation at nucleotide 30875 as numbered in the Yoshitake et al. (1985) reference. The lane numbers and mutations follow. 1: C30875T; 2: A30897G; 3: 30905 ΔG; 4: 30918 ΔA; 5: A30918G; 6: C30928A; 7: A30929T; 8: T30930C; 9: C30935T; 10: T30936G; 11: T30945C; 12: G30950T; 13: 30969 ΔGC; 14: A30972G; 15: G30992A; 16: G31001T; 17: C31008T; 18: G31029A; 19: T31039A; 20: T31041C; 21: G31047A; 22: G31052A; 23: C31077A; 24: C31091T; 25: C31118T; 26: T31127A; 27: C31140G; 28: T3112G; 29: G31203T.

ddF gels were performed under two conditions—PAGE/TRI/20° C. and PAGE/CAP/20° C. (see FIGS. 2A and 2B). For exon H, the average SSCP efficiencies for the 24 substitutions analyzed were 91% and 72% for the two conditions, respectively. The efficiencies for individual mutations varied with the conditions; i.e., the efficiency for sample 6 was 98% and 7%, respectively, and the efficiency for sample 13 was 100% and 3%, respectively. Of the 24 samples with single-base substitutions, 4% and 25% had efficiencies of less than 20%; 17% and 25% had efficiencies from 21%–80%; and 79% and 50% had efficiencies greater than 81% (shown in FIGS. 2A and 2B, respectively). The efficiencies under the two conditions for each mutation in exon H were plotted (FIG. 2C) and were poorly correlated (correlation coefficient=0.39 and the 99% confidence interval overlaps with zero). Correlation coefficients are determined by calculating the efficiency of the SSCP component for each mutation under a first set of conditions and then calculating the efficiency under a second set of conditions and then correlating these using Microsoft Excel 97 software.

Seventeen selected single-base substitutions in exon H and 16 selected single-base substitutions in exons B/C were chosen for further testing, because the efficiency of the SSCP component under standard conditions is low in exon B/C but is high in exon H. A variety of electrophoretic conditions were tested, which include gel matrices of MDE™ (BioWhittaker Molecular Applications, Rockland, Me. USA, HR1000, (Genomyx, Foster City, Calif. USA) (AMERESCO, Solon, Ohio, USA) and (Bio-Rad Laboratories, Hercules, Calif. USA); running buffers of TBE (pH 8.3), CAP which is a high pH buffer (pH 9.6) and TRI which is a medium pH buffer (pH 7.9); additives of glycerol, urea, Resolver Gold™ and PEG; and temperatures at 20° C. and 8° C. Under each condition, the efficiency of the SSCP component was scored for each mutation and for each region.

The average efficiency of the SSCP component for the 17 mutations from exon H and the 16 mutations from exon B/C was utilized to estimate the overall sensitivity of seven sets of conditions (Table 1). The averages are derived from analysis of about 1,500 mutation-containing segments. The average efficiencies varied with the regions analyzed and the conditions. Correlation coefficients (R) also varied with the regions analyzed and the conditions (Table 2). The effects of changing only buffer (1×2 (condition 1 compared with condition 2) and 4×5), of only temperature (2×3), of only matrix (2×4), of both temperature and glycerol (5×7) and of both buffer and glycerol (6×7), are among the changes that can be assessed in Table 2. Some

TABLE 1

Average Efficiency of the SSCP Component

Average SSCP efficiency[a] (%) under each condition

| Genomic region[b] | 1 PAGE TRI 20° C. (III)[c,d] | 2 PAGE CAP 20 C. | 3 PAGE CAP 8° C. (I) | 4 HR CAP 20° C. | 5 HR TBE 20° C. | 6 HR TRI 8° C. (V) | 7 HR TBE 8° C. Gly (II) |
|---|---|---|---|---|---|---|---|
| Exon H | 89 | 61 | 93 | 51 | 78 | 90 | 75 |
| Exons B/C | 59 | 44 | 87 | 57 | 62 | 89 | 91 |

[a]Approximately 1,500 segments with mutated sequence were analyzed under each condition. Per sample, the number of mutated segments ranged from 1–46 segments.
[b]There are 17 substitution mutations in exon H and 16 substitution mutations in exons B/C, which are selected due to low efficiency of the SSCP component.
[c]PAGE = 10% PAGE[plus] gel, HR = 10% HR 1000 gel. TRI = 30 mM Triethanolamine/Tricine buffer (pH 7.9), CAP = 30 mM Ethanolamine/CAPSO (pH 9.6), TBE = 50 mM Tris/Boric acid (pH 8.3). Gly = 2.5% Glycerol.
[d]The boldface electrophoresis conditions are those selected for the blinded analysis of the factor IX gene. Condition IV is not shown because it was tested in subsequent experiments.

TABLE 2

The Correlation Coefficient (R) of the Efficiencies of SSCP Component between Each Two Conditions in Exons H and B/C[a]

| Electrophoresis condition | | | | | | | |
|---|---|---|---|---|---|---|---|
| 1 | PAGE TRI 20° C. (III)[b] | X | | | | | |
| 2 | PAGE CAP 20° C. | 0.30/ 0.74[c] | X | | | | |
| 3 | PAGE CAP 8° C. (I) | 0.77/ −0.09 | 0.35/ 0.10 | X | | | |
| 4 | HR CAP 20° C. | 0.45/ 0.63 | 0.63/ 0.60 | 0.39/ −0.15 | X | | |
| 5 | HR TBE 20° C. | 0.43/ 0.62 | 0.69/ 0.77 | 0.60/ 0.33 | 0.63/ 0.74 | X | |
| 6 | HR TRI 8° C. (V) | 0.26/ −0.35 | 0.53/ −0.16 | 0.34/ 0.74 | 0.42/ −0.06 | 0.76/ 0.04 | X |
| 7 | HR TBE 8° C. Gly (II) | 0.33/ 0.35 | 0.34/ 0.19 | 0.27/ −0.25 | 0.52/ 0.19 | 0.28/ −0.34 | −0.14/ −0.27 |
| | | PAGE TRI 20° C. (III) | PAGE CAP 20° C. | PAGE CAP 8° C. (I) | HR CAP 20° C. | HR TBE 20° C. | HR TRI 8° C. (V) |
| | | 1 | 2 | 3 | 4 | 5 | 6 |

Electrophoresis condition

[a]There are 17 substitution mutations in exon H and 16 substitution mutation in exons B/C under each electrophoresis condition.
[b]The boldcase electrophoresis conditions are finally selected for the blinded analysis.
[c]R is indicated in order of exon H/exon B/C.

of the correlation coefficients were negative, implying that given samples of low efficiency under one condition were preferentially of higher efficiency under the second condition. Glycerol and temperature seemed to be the factors that produced the greatest changes in mobility pattern.

Five conditions for SSCP were selected after analysis of 22 conditions (not all data shown). These five conditions were judged to provide sufficient redundancy to detect virtually all sequence changes. Four of these five conditions are shown in Tables 1 and 2 (see boldface conditions). These conditions were selected as having both reasonably high average SSCP efficiencies (Table 1) and low correlations or negative correlations for both exons H and B/C.

EXAMPLE 2

Blinded Analysis of $SSCP_5$

The five selected conditions were tested by a blinded analysis in which the eight exons and associated splice junctions of the factor IX gene were scanned in one lane (Table 3A). Blinded analysis was performed with 100 samples, including 50 samples with an unknown number of hemizygous mutations in the factor IX gene, and 50 samples with an unknown number of heterozygous mutations in the factor IX gene. The eight exons and their splice sites were amplified by 15 pairs of primers: in exon A: F9(-121)-20D and F9(49)-20U, and F9(9)-20D and F9(157)-21U; in exons B/C: F9(6242)-22D and F9(6536)-21U, F9(6476)-21D and F9(6736)-23U, and F9(6242)-22D and F9(6736)-23U; in exon D: F9(10299)-20D and F9(10537)-22U; in exon E: F9(17633)-22D andF9(17843)-23U; in exon F: F9(20315)-21D and F9(20457)-24U, F9(20392)-21D and F9(20648)-21U; in exon G: F9(2991)-22D and F9(30219)-23U; in exon H: F9(30746)-20D and F9(31026)-21U, F9(30969)-20D and F9(31167)-22U, F9(31079)-21D and F9(31305)-21U, F9(31262)-20D and F9(31429)-20U, F9(32637)-20D and F9(32827)-20U. Each PCR was performed with 94° C. for 15 seconds, 55° C. for 30 seconds, and 72° C. for one minute for 30 cycles. The PCR was hot-started at 94° C. for ten minutes and ended with an additional ten minutes at 72° C. The PCR mixture contained a total volume of 5 μL of 50 mM KCl, 10 mM Tris/HCl, pH 8.3, 2.5 mM MgCl$_2$, 20 μM of dATP and 200 μM of each other dNTP, 0.6 μCi [α-$^{33}$P]-dATP (Amersham Life Science, >2500 Ci/mmol, 10 mCi/mL), 0.4 μM of each primer, 0.2 units of TaqGold, 200 ng genomic DNA. The PCR reactions were mixed with a four-fold volume of the stop buffer.

TABLE 3

Summary of Blinded Analysis

A. Individual SSCP Sensitivity

|  | Individual condition | | | | |
|---|---|---|---|---|---|
|  | PAGE CAP 8° C. (I) | HR TBE 8° C. Gly (II) | PAGE TRI 20° C. (III) | PAGE TBE 20° C. Gly (IV) | HR TRI 8° C. (V) |
| Sensitivity[a] (%) | 79 | 87 | 65 | 89 | 65 |

B. Observed Joint SSCP Sensitivities

|  | Observed sensitivity for all possible groups of conditions[b] (%) | | | |
|---|---|---|---|---|
|  | 2 joint conditions (10 sets) | 3 joint conditions (10 sets) | 4 joint conditions (5 sets) | 5 joint conditions (1 set) |
| Best Group | 95 | 100 | 100 | 100 |
| Worst Group | 85 | 89 | 94 | 100 |

C. The distribution of hits under all the five conditions

|  | The number of hits for a given mutation | | | | | |
|---|---|---|---|---|---|---|
|  | 0 | 1 | 2 | 3 | 4 | 5 |
| Mutations (%) | 0 | 10 | 8 | 8 | 30 | 44 |

[a]The individual sensitivity was calculated under each set of conditions and we took each sense and antisense pair of segments as a unit for calculation of sensitivity.
[b]The observed joint sensitivities (%) were caluclated under two-, three-, four- and five-sets of conditions, which had ten, ten, five and one possible combinations, respectively. The best scores were obtained under two conditions of II and IV; under three conditions of II and IV and any of I, III, and V; under four conditions of II and IV and any two of I, III, and IV. The worst scores were obtained under two conditions of III and V; under three conditions of III and V and I; under four conditions of III and V and I and IV.

Fifteen PCR segments of the factor IX gene were amplified, ranging in size from 143–295 nucleotides. In total, all 84 single-base substitutions throughout all the 15 PCR segments were detected by SSCP$_5$. In retrospect, all of the mutations could have been detected by a combination of the three best conditions (Table 3B). However, the idiosyncratic nature of SSCP dictates that one cannot predict, a priori, which combinations of conditions will be the best. There is sufficient redundancy, such that the worst combination of conditions required the five conditions. Almost 75% of the mutations were detected in at least four of the five conditions. Ten percent of the mutations were detected with only one of the five conditions (Table 3C).

A prospective analysis was performed on the factor VIII gene in patients with hemophilia A. Forty-eight amplicons were amplified to cover the 26 exons and their splicing sites, ranging in size from 140 to about 300 bp in length. These amplicons were divided into three groups of 16 products per lane. Five electrophoresis conditions were chosen, as per the blinded analysis in the factor IX gene. Shifted segments relative to a wild type control were scored for each sample under each condition. Sequencing analysis was performed on segments containing putative mutations to confirm that the shifted segments each contain a mutation. Those without shifted segments under all five conditions were sequenced in their entirety to determine whether a mutation was missed.

Eighty-nine patient samples were analyzed by multi-conditional SSCP and sequencing analysis (three samples were not analyzed due to large deletions). Mutations were found in 86 of the 89 samples and they were scattered along the amplicons. Of the 3 samples for which a mutation was not found, one sample (1.1%) showed a slightly shifted segment which was scored by the multi-conditional SSCP thereby resulting in a false positive. The absence of a mutation was confirmed by sequencing. The remaining two samples showed no shifts in segments and no mutations were seen by sequence analysis. The finding of 86 of 86 mutations shows that the conditions used had 100% sensitivity. The one false positive and no false negatives show that the specificity was 99%. These results are shown in Table 4.

More data are required to determine whether one or a few percent of mutations might be missed when SSCP$_5$ is applied to other genes. However, past experience with ddF and restriction endonuclease fingerprinting (REF) (Liu and Sommer, 1995) and with the very large statistical sample size that underlies this analysis (1,500 mutation-containing segments per condition) suggest that the sensitivity of SSCP$_5$ will be very high, perhaps 99% or greater. If only four conditions had been utilized in the blinded analysis, the sensitivity would have decreased to 94–100%, depending on which condition was dropped.

TABLE 4

Summary of Prospective Analysis

|  |  | Multi-conditional SSCP | |
|---|---|---|---|
|  |  | Shifted segment | No shifted segment |
| Sequencing analysis | Mutation found | 86 | 0 |
|  | No mutation found | 1 | 2 |

EXAMPLE 3

Electrophroesis

Non-denatuing gels (45 cm×37.5 cm×0.4 mm) were electrophoresed by using a Poker Face SE 1500 sequencing apparatus at 12 W constant power or a Bio-Rad Sequi-Gen GT sequencing cell (50 cm×38 cm×0.4 mm) at 15 W constant power at 20° C. or at 8° C. Gel matrices were selected from 10% MPE™, 10% HR1000, 10% PAGE$^{plus}$, and 10% Dcode™. Running buffers were selected from 50 mM TBE (50 mM each of Trizma base and Boric acid, pH 8.3 at 25° C.), 30 mM CAP (30 mM each of Ethanolamine and CAPSO (3-[cyclohexylamino]-2-hydroxy-1-propanesulfonic acid), pH 9.6 at 25° C.), and 30 mM TRI (30 mM each of Triethanolamine (2,2',2"-nitrilotriethanol) and Tricine (N-tri[hydroxymethyl]methylglycine), pH 7.9 at 25° C.). Additives were glycerol, urea, Resolver Gold™, and PEG. After a pre-electrophoresis for 30 minutes, 1.5 μL of sample was loaded and electrophoresed for 6–16 hours. The gel was dried and autoradiographed with Kodak BioMax MR film.

EXAMPLE 4

Gel Analysis

On the ddF gel, an informative dideoxy component was easily detected by a missing segment or an extra segment. The mutation-containing segments showing altered mobilities in the SSCP component were scored and compared with a wild type control. In the blinded analysis, 30 single-stranded segments (15 double-stranded PCR products), covering the eight exons were scored by comparison with their neighbors. Unequivocal mobility changes were scored. Typically, a migration change of ½ band width on the upper part of the gel or ¼ band width on the lower part was the limit of resolution.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Glavac D and Dean M (1993). *Hum. Mutat.* 2:404–414.
Hayashi K and Yandell DW (1993). *Hum. Mutat.* 2:338–346.
Hongyo T, et al. (1993). *Nucl. Acids Res.* 21:3637–3642.
Liu Q and Sommer SS (1994). *PCR Methods and Applications* 4:97–108.
Liu Q and Sommer SS (1995). *BioTechniques* 18:470–477.
Liu Q and Sommer SS (1998). *BioTechniques* 25:50–56.
Liu Q, et al. (1996). *Hum. Mol. Genet.* 5:107–114.
Michaud J, et al. (1992). *Genomics* 13:389–394.
Sarkar G, et al. (1992a). *Nucl. Acids Res.* 20:871–878.
Sarkar G., et al. (1992b). *Genomics* 13:441–443.
Sheffield VC, et al. (1993). *Genomics* 16:325–332.
Takahashi-Fujii A, et al. (1993). *PCR Methods and Applications* 2:323–327.
Yoshitake S, et al. (1985). *Biochemisty* 24:3736–3750.

What is claimed is:

1. A method for determining a combination of sets of electrophoresis parameters which are useful in an SSCP analysis for maximizing the number of different mutations in a nucleic acid sample which can be detected using a combination of said sets of electrophoresis parameters wherein said SSCP analysis comprises running two or more gels using a different set of electrophoresis parameters with each gel wherein said method comprises:
   a) performing SSCP analysis on said nucleic acid sample using multiple sets of electrophoresis parameters,
   b) calculating SSCP efficiencies,
   c) calculating a correlation coefficient of efficiencies, and
   d) determining which of the multiple sets of electrorhoresis parameters yield the highest average efficiencies and the lowest correlation coefficients of the sets,
   wherein the most useful combinations of sets of electrophoresis parameters of the multiple sets are those having the highest average SSCP efficiencies and the lowest or most negative correlation coefficients.

2. The method of claim 1 wherein said parameters are selected from the group consisting of gel matrix, running buffer, additive and temperature.

3. The method of claim 2 wherein said gel matrix is selected from the group consisting of PAGE$^{plus}$, MDE™, HR1000 and Dcode™.

4. The method of claim 2 wherein said gel matrix is selected from the group consisting of PAGE$^{plus}$ and HR1000.

5. The method of claim 2 wherein said running buffer is selected from the group consisting of TBE, CAP and TRI.

6. The method of claim 2 wherein said additive is selected from the group consisting of glycerol, urea, Resolver Gold™ and PEG.

7. The method of claim 2 wherein said additive is glycerol.

8. The method of claim 2 wherein said temperature is selected from the group consisting of 8° C. and 20° C.

9. The method of claim 1 wherein said SSCP analysis is performed in conjunction with dideoxy fingerprinting, bidirectional dideoxy fingerprinting, or restriction endonuclease fingerprinting.

10. The method of claim 1 wherein a high average SSCP efficiency is an average efficiency greater than 50%.

11. The method of claim 1 wherein a high average SSCP efficiency is an average efficiency greater than 70%.

12. The method of claim 1 wherein a high average SSCP efficiency is an average efficiency greater than 90%.

13. The method of claim 1 wherein a low correlation coefficient is a value lower than 0.4.

14. A method of analyzing for mutations by performing multiconditional SSCP, said method comprising:
   i) providing a single-stranded nucleic acid to be analyzed,
   ii) providing a single-stranded control nucleic acid;
   iii) electrophoresing said single stranded nucleic acid to be tested and said single-stranded control nucleic acid on two or more nondenaturing gels using electrophoresis conditions selected from the group consisting of:
      a) PAGE, TRI, 20° C.; b) PAGE, CAP, 20° C.; c) PAGE, CAP, 8° C.; d) HR, CAP, 20° C.; e) HR, TBE, 20° C.; f) HR, TRI, 8° C.; g) HR, TBE, 8° C., glycerol; and h) PAGE, TBE, 20° C., glycerol, wherein electrophoresis is performed using two or more of said electrophoresis conditions;
   iv) determining a distance said nucleic acid to be analyzed migrates on each gel;
   v) determining a distance said control nucleic acid migrates on each gel; and
   vi) comparing the distance said nucleic acid to be analyzed migrates on a gel with the distance said nucleic acid control migrates on the same gel;
   wherein if the nucleic acid to be analyzed migrates a different distance on any one or more gels than does the control nucleic acid on the same gel, then said nucleic acid to be analyzed has a mutation as compared to said control nucleic acid.

15. The method of claim 14 wherein said mutations are in a gene for factor IX.

16. The method of claim 14 wherein said mutations are in a gene for factor VIII.

17. A method of analyzing for mutations by performing multiconditional SSCP, said method comprising:
   i) providing a single-stranded nucleic acid to be analyzed,
   ii) providing a single-stranded control nucleic acid;
   iii) electrophoresing said single stranded nucleic acid to be tested and said single-stranded control nucleic acid on two or more nondenaturing gels using electrophoresis conditions selected from the group consisting of:
      a) PAGE, CAP, 8° C.; b) HR, TBE, 8° C., glycerol; c) PAGE, TRI, 20° C.; d) PAGE, TBE, 20° C., glycerol; and e) HR, TRI, 8° C., wherein electrophoresis is performed using two or more of said electrophoresis conditions;
   iv) determining a distance said nucleic acid to be analyzed migrates on each gel;

v) determining a distance said control nucleic acid migrates on each gel; and vi) comparing the distance said nucleic acid to be analyzed migrates on a gel with the distance said nucleic acid control migrates on the same gel;

wherein if the nucleic acid to be analyzed migrates a different distance on any one or more gels than does the control nucleic acid on the same gel, then said nucleic acid to be analyzed has a mutation as compared to said control nucleic acid.

18. The method of claim 17 wherein said mutations are in a gene for factor IX.

19. The method of claim 17 wherein said mutations are in age for factor VIII.

* * * * *